United States Patent [19]

Lok et al.

[11] Patent Number: 4,842,836

[45] Date of Patent: Jun. 27, 1989

[54] ZEOLITE LZ-133

[75] Inventors: Brent M. Lok, New City; Thomas R. Cannan, Valley Cottage; Edith M. Flanigen, White Plains, all of N.Y.

[73] Assignee: UOP

[21] Appl. No.: 843,295

[22] Filed: Mar. 24, 1986

Related U.S. Application Data

[63] Continuation-in-part of Ser. No. 363,109, Mar. 29, 1982, abandoned.

[51] Int. Cl.$^4$ .............................................. C01B 33/28
[52] U.S. Cl. ..................................................... 423/328
[58] Field of Search ............ 423/328 C, 328 T, 329 T

[56] References Cited

U.S. PATENT DOCUMENTS

| | | | |
|---|---|---|---|
| 3,298,780 | 1/1967 | Fleck | 423/328 C |
| 3,411,874 | 11/1968 | Ciric | 423/328 C |
| 3,459,676 | 8/1969 | Kerr | 423/328 T |
| 3,702,886 | 11/1972 | Argauer et al. | 423/328 |
| 4,081,490 | 3/1978 | Plank et al. | 423/328 T |
| 4,086,186 | 4/1978 | Rubin et al. | 423/329 |
| 4,247,416 | 1/1981 | Doherty et al. | 423/328 T |
| 4,331,643 | 5/1982 | Rubin et al. | 423/329 T |
| 4,366,135 | 12/1982 | Le Van Mao et al. | 423/329 |
| 4,372,930 | 2/1983 | Short et al. | 423/326 |

FOREIGN PATENT DOCUMENTS

| | | | |
|---|---|---|---|
| 0057016 | 8/1982 | European Pat. Off. | 423/329 T |
| 0091048 | 10/1983 | European Pat. Off. | 423/328 T |
| 0091049 | 10/1983 | European Pat. Off. | 423/328 T |
| 0105679 | 4/1984 | European Pat. Off. | 423/328 T |
| 0007816 | 1/1982 | Japan | 423/328 T |

*Primary Examiner*—John Doll
*Assistant Examiner*—R. Bruce Breneman
*Attorney, Agent, or Firm*—Richard G. Miller

[57] ABSTRACT

A novel crystalline aluminosilicate composition denominated "zeolite LZ-133" or simply "LZ-133" and having uniform pore dimensions of approximately 4.3 Angstroms is prepared hydrothermally from a reaction mixture containing as essential reagents, water, alkali or alkaline earth metal oxide, alumina, silica and a quaternary ammonium compound.

8 Claims, No Drawings

ZEOLITE LZ-133

RELATED APPLICATIONS

This application is a continuation-in-part of pending application Ser. No. 363,109, filed Mar. 29, 1982 now abandoned.

The present invention relates in general to aluminosilicate compositions and to the method for their preparation. More particularly the invention relates to novel crystalline aluminosilicates of the zeolite type prepared hydrothermally from a reaction mixture comprising an alkali or an alkaline earth metal oxide, silica, alumina, water and methylquinuclidine ions.

In the synthesis of zeolite species, particularly those which are highly siliceous, from reaction mixtures which contain organic nitrogeneous or phosphonium bases, it has been speculated that these relatively large ionic species serve, at least in part, as templating agents which influence the topology of the crystalline zeolite product. It is apparent, however, that other factors in the synthesis process also influence the structure of the zeolite product since it is known that the same zeolite species can be produced from reaction mixtures containing quite different organic bases, and also that gels containing the same organic base can produce substantially different zeolite structures. For example, both tetraethylammonium and tetrabutylammonium ions can template the formation of zeolite ZSM-11 (U.S. Pat. No. 3,709,979), whereas tetraethylammonium ions can also template the formation of zeolite Beta (U.S. Pat. No. 3,308,069). Since there are a number of variable parameters in the synthesis process, it is usually quite difficult to determine precisely which particular value of which particular parameter or parameters are determinative of the structure of the crystallized product. Frequently, more than one zeolite species is produced in a given synthesis.

As reported in our copending application Ser. No. 363,110, filed Mar. 29, 1982, methylquinuclidine ion is capable of templating the formation of a novel zeolite species, denominated LZ-132, from a reaction mixture containing same in combination with water, soda, alumina and silica. LZ-132 is topologically related to the mineral levynite and also to the synthetic zeolite species ZK-20.

We have further found that the same reaction mixture which produces LZ-132 also produces another novel zeolite species, denominated LZ-133, whose crystal structure is as yet unknown, but is likely to be topologically related to LZ-132, ZK-20 and levynite. The X-ray powder diffraction pattern of LZ-133, however, clearly establishes it as a distinct zeolite species.

The mineral zeolite levynite has been known since 1825 and has an idealized chemical composition expressed in terms of mole ratios of oxides as $CaO:Al_2O_3 4SiO_2 6H_2O.$ Levynite's crystal symmetry is hexagonal with unit cell parameters $a_o=13.32$ A and $c_o=22.51$ A. The X-ray powder diffraction pattern of levynite is given in "Zeolite Molecular Sieves", D. W. Breck, Wiley (1974) as set forth in Table I, below.

TABLE I

| d(A) | I | d(A) | I |
|---|---|---|---|
| 10.4 | 35 | 2.725 | 6 |
| 8.19 | 65 | 2.634 | 40 |
| 7.69 | 18 | 2.593 | 6 |
| 6.72 | 18 | 2.534 | 16 |
| 5.64 | 4 | 2.453 | 2 |
| 5.19 | 30 | 2.406 | 16 |
| 4.28 | 50 | 2.303 | 10 |
| 4.10 | 100 | 2.256 | 4 |
| 3.87 | 20 | 2.234 | 14 |
| 3.84 | 6 | 2.136 | 18 |
| 3.61 | 6 | 2.113 | 2 |
| 3.49 | 16 | 2.072 | 6 |
| 3.46 | 6 | 2.050 | 4 |
| 3.35 | 14 | 1.981 | 2 |
| 3.17 | 50 | 1.960 | 6 |
| 3.10 | 20 | 1.896 | 6 |
| 2.882 | 10 | | |
| 2.861 | 10 | | |
| 2.815 | 80 | | |

ZK-20 is described and claimed in U.S. Pat. No. 3,459,676 issued Aug. 5, 1969 to G. T. Kerr. ZK-20 is prepared hydrothermally using an organic cation as a templating agent, namely the 1-methyl-1-azonia-4-azabicyclo(2,2,2)octane ion, and has an as-synthesized chemical composition, in terms of mole ratios of oxide, of:

$0.1-0.02R_2O:0.8-0.9Na_2O:Al_2O_3:4-5\ SiO_2:1-5H_2O.$ wherein "R" is the ion used as the templating agent. Its X-ray powder diffraction is set forth in Table II, below

TABLE II

| d(A) | I | d(A) | I |
|---|---|---|---|
| 14.2 | VW | 2.41 | M |
| 10.4 | | 2.23 | W-M |
| 9.5 | W | 2.18 | VW |
| 8.2 | S | 2.14 | M |
| 7.7 | W | 2.07 | VW |
| 6.7 | M | 2.04 | W |
| 5.2 | S | 1.96 | W |
| 4.3 | S | 1.93 | W |
| 4.1 | VS | 1.90 | W |
| 3.86 | M-S | 1.88 | VW |
| 3.62 | W | 1.86 | W |
| 3.48 | W | 1.80 | M |
| 3.34 | W | 1.69 | W |
| 3.18 | S | 1.68 | M |
| 3.10 | M | 1.60 | M |
| 2.87 | M | 1.555 | M |
| 2.81 | S-VS | 1.545 | M |
| 2.64 | M | 1.435 | M |
| 2.59 | VW | 1.400 | M |
| 2.52 | W | | | wherein with respect to the intensity values, "I", "VW" represents Very Weak; "W" represents Weak; "M" represents Medium; "S" represents Strong and "VS" represents Very Strong. These intensity value symbols have the same meaning when used hereinafter with respect to any X-ray powder diffraction data concerning this or other crystalline materials.

Zeolite LZ-133, the novel aluminosilicate zeolite species or the present invention, differs substantially in its chemical composition from either of the aforesaid ZK-20 and levynite materals as well as having a distinguishing X-ray powder diffraction pattern. LZ-133 has a chemical composition expressed in terms of mole ratios of oxides as:

$x\ M_{2/n}O:Al_2O_3:y\ SiO_2:z\ H_2O$ wherein "M" is at least one cation having the valence "n", "x" has a value of from zero to 3.5, "y" has a value of from 10 to 80, preferably 15 to 50 and "z" has a value of from zero to 15, preferably zero to 5, said aluminosilicate having an X-ray powder diffraction pattern containing at least the d-spacings of Table III or Table IV below.

Standard techniques were employed to obtain the data of Table III and all other X-ray data for LZ-133 appearing hereinafter. The radiation was the K-alpha doublet of copper, and a Geiger-counter spectrometer with a strip-chart pen recorder was employed. The peak heights and their positions as a function of 2 times theta, where theta is the Bragg angle, were read from the spectrometer chart and the interplanar spacings in Angstroms corresponding to the recorded lines were determined.

As synthesized, the chemical composition of LZ-133 in terms of mole ratios of oxides is a $Q_{2/n}O$:b $R_2O$:$Al_2O_3$:c $SiO_2$:d $H_2O$ wherein "a" has a value in the range of 0.1 to 1.5, Q is an alkali metal or alkaline earth metal cation having the valence "n", "b" has a value in the range or 0.5 to 2.5, the value of (a+b) is from 0.9 to 3.5, R represents the methylquinuclidine ion, "c" has a value of from 10 to 80 preferably 15 to 50, and "d" has a value of from zero to about 15, depending upon the degree or dehydration and the degree to which the intracrystalline pore volume is occupied by the organic or metal cation species. The as-synthesized form of the zeolite, which can include the dehydrated (activated) form, but not the form which results from ion exchange or calcination at a temperature sufficiently high, i.e., at least 400° C., but preferably 500° C.-650° C., to decompose the organic constituents, has a characteristic X-ray powder diffraction pattern which contains at least the d-spacings set forth in Table III below:

TABLE III

| 2 theta | d(A) | Relative Intensity |
|---|---|---|
| 13.5 ± 0.2 | 6.66 — 6.46 | M |
| 13.7 ± 0.2 | 6.56 — 6.37 | M |
| 14.2 ± 0.2 | 6.33 — 6.15 | M |
| 17.3 ± 0.3 | 5.21 — 5.04 | M |
| 19.2 ± 0.3 | 4.70 — 4.55 | VS |
| 19.7 ± 0.2 | 4.55 — 4.46 | M |
| 24.3 ± 0.3 | 3.71 — 3.62 | S |
| 25.7 ± 0.2 | 3.49 — 3.44 | M |
| 27.3 ± 0.2 | 3.29 — 3.24 | M |
| 27.9 ± 0.3 | 3.23 — 3.16 | M |
| 28.5 ± 0.2 | 3.15 — 3.11 | M |
| 29.6 ± 0.2 | 3.04 — 3.00 | M | and does not contain a d-spacing within the range of 4.01–4.03 A.

The organic cations of the as-synthesized zeolite are not considered to be ion-exchangable in the ordinary sense due to steric considerations of the crystal structure, the organic cations themselves and the positions occupied by these cations within the crystal lattice. These large organic cations, moreover, tend to block the pore system and prevent the normal passage of the smaller metal cation species into and out of the crystal structure by the conventional ion-exchange mechanism. It is possible, however, to thermally or chemically decompose the organic cation species as well as any occluded organic moieties to molecular or atomic fragments small enough to be removed through the pore system. The organic cations associated with $AlO_4$ tetrahedra can be converted by this procedure to ammonium or hydrogen cations which are ion-exchangable in the usual manner. Calcination of the as-synthesized zeolite in air at a temperature of at least 400° C., preferably 500° C. to 650° C. for one hour, is sufficient to create the methylquinuclidine-free decationized form. Lower temperatures and/or shorter calcination periods are required to accomplish this result if the calcination is carried out under vacuum conditions.

As will be readily apparent to those skilled in this art, the ratio of the combined organic metallic cations to framework aluminum can appear to be substantially higher in the as-synthesized form of the zeolite than stoichiometric considerations based on conventional zeolite chemistry would permit. This phenomenon is not unique to LZ-133, however, and has generally been observed in high-silica zeolites synthesized from an organic-containing system. While the exact condition of each organic and metal cationic moiety of the zeolite are not known, it can be theorized that at least some of the organic species are merely occluded in the structure, and in addition entrap alkali or alkaline earth species which are not present in association with $AlO_4$ tetrahedra. In any event there is no doubt that the topology of LZ-133 is essentially zeolitic.

It is further noted that upon calcination at temperatures sufficiently high to decompose the organic species present, the X-ray powder diffraction pattern of LZ-133 changes somewhat. The most notable changes appear in the intensity values for a number of d-spacings. Some shifting in line positions are also noted as well as the appearance or disappearance of one or more lines attributed to the removal of the organic species. These changes do not, however, indicate a change in the basic topology of the zeolite structure, the X-ray powder diffraction pattern of which contains at least the d-spacings set forth in Table IV below:

TABLE IV

| 2 theta | d(A) | Relative Intensity |
|---|---|---|
| 13.5 ± 0.2 | 6.66 — 6.46 | S |
| 13.7 ± 0.2 | 6.56 — 6.37 | S |
| 14.2 ± 0.2 | 6.33 — 6.15 | S |
| 17.3 ± 0.3 | 5.21 — 5.04 | W |
| 19.2 ± 0.3 | 4.70 — 4.55 | S |
| 19.7 ± u.2 | 4.55 — 4.46 | M |
| 24.3 ± 0.3 | 3.71 — 3.62 | MS |
| 25.7 ± 0.2 | 3.49 — 3.44 | M |
| 27.3 ± 0.2 | 3.29 — 3.24 | M |
| 27.9 ± 0.3 | 3.23 — 3.16 | M |
| 28.5 ± 0.2 | 3.15 — 3.11 | M |
| 29.6 ± 0.2 | 3.04 — 3.00 | | and does not contain a d-spacing within the range of 4.01–4.03 A.

The organic-free form of the zeolite, such as prepared by the calcination of as-synthesized LZ-133 described above, either per se or after subsequent ion-exchange, has the chemical composition in the anhydrous state in terms of mole ratios or oxides x $M_{2/n}O$:$Al_2O_3$:y $SiO_2$ wherein "M" is an ammonium, hydrogen or metal cation, "x" has a value of zero to 1.1, "y" has a value of 10 to 80, preferably 15 to 50, said zeolite having an X-ray powder diffraction pattern containing at least the d-spacings set forth in Table IV, supra, and no d-spacings in the range of 4.01–4.03A.

As indicated hereinbefore, LZ-133 and LZ-132 are generally produced together as co-crystallization products from the same reaction gel. The proportions of each species produced is dependent upon the value of the various process parameters involved. It appears that the use of silica sols as the silica source in the reaction mixture, lower reaction temperature and longer crystallization times tend to to favor the production of LZ-132, possibly by the reconversion of previously formed LZ-133 which is favored by relatively higher reaction temperatures, shorter crystallization times and the use of precipitated amorphous silica as the principal silica source in the reaction gel.

Accordingly zeolite LZ-133 can be prepared hydrothermally by crystallization from a gel whose composition expressed in terms of mole ratios of oxides falls within the following ranges:

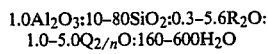
1.0Al$_2$O$_3$:10–80SiO$_2$:0.3–5.6R$_2$O:
1.0–5.0Q$_{2/n}$O:160–600H$_2$O wherein "R" represents the methylquinuclidine ion, "Q" represents an alkali metal or alkaline earth cation, preferably an alkali metal cation such as sodium, potassium or cesium, and "n" is the valence of the said metal cation. Preferably, the gel composition expressed in terms or mole ratios of oxides should fall within the following ranges.

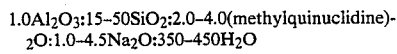
1.0Al$_2$O$_3$:15–50SiO$_2$:2.0–4.0(methylquinuclidine)-
$_2$O:1.0–4.5Na$_2$O:350–450H$_2$O In preparing the aqueous reaction mixture the conventional reactants used in zeolite synthesis are suitably employed. Alumina can be obtained from activated alumina, alpha alumina, gamma alumina, boehmite, pseudo-boehmite, alumina trihydrate, aluminum hydroxide or sodium aluminate. Silica can be obtained from precipitated silica, sodium silicates, silica sol, or silica aerogel, preferably precipitated silica.

Advantageously, the crystallization procedure is carried out at temperatures in the range of from about 100° C. to 200° C., preferably at 125° C. to 150° C., the pressure being autogenous pressure, until the product is crystallized. The crystalline product is then filtered, washed and dried.

The method for preparing zeolite LZ-133 is illustrated by the following examples.

EXAMPLE 1

(a) Preparation of methylquinuclidine hydroxide (MeQOH).

Initially 126.2 grams of quinuclidine (1-azabicyclo(2,2,2)octane) were dissolved in 126.2 grams or water in a one-liter 3-neck round-bottom flask fitted with a condenser, a thermometer and a mechanical glass stirring rod with an inert plastic crescent stirring blade. Using a constant dropping funnel, 162.5 grams of methyl iodide (CH$_3$I) were slowly added into the quinuclidine solution with vigorous mixing. A temperature rise of 53° C. was observed. After the completion of the addition of methyl iodide solution, the entire solution was mixed vigorously for another 20 hours. A total of about 415 grams of solution product was recovered (Calc. 69.5 wt.-% MeQI). The product was chemically analyzed to have 3.6 wt.-% nitrogen and 26.1 wt.-% carbon (C/N ratio=8.5; theoretical C/N ratio=8.0)

(b) Preparation of LZ-133

To a beaker were added with mixing and in the order named, 70.5 grams of distilled water, 24.8 grams of a precipitated amorphous silica containing 84.2 wt.-% SiO$_2$, and 27.2 grams of methylquinuclidine iodide. Thereafter 3.8 grams of distilled water were heated with stirring in a beaker to form a not sodium aluminate solution which was then added to the previously prepared silicamethylquinuclidine gel along with 10 grams of water used to rinse the beaker wherein the sodium aluminate solution was prepared. The resulting final reaction gel was thoroughly mixed and had a molar oxide composition of:

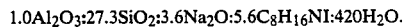
1.0Al$_2$O$_3$:27.3SiO$_2$:3.6Na$_2$O:5.6C$_8$H$_{16}$NI:420H$_2$O.

The synthesis gel was then placed in a polytetrafluoroethylene container which in turn was sealed in a stainless steel pressure vessel and digested at 200° C. for 45 hours. The solid reaction product was recovered by filtration, washed with water and dried at ambient temperature. The product was identified by X-ray diffraction as zeolite LZ-133. The chemical composition of the product from a repeated synthesis is as follows:

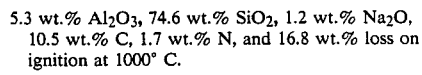
5.3 wt.% Al$_2$O$_3$, 74.6 wt.% SiO$_2$, 1.2 wt.% Na$_2$O,
10.5 wt.% C, 1.7 wt.% N, and 16.8 wt.% loss on
ignition at 1000° C.

The anhydrous chemical composition expressed in terms of oxide mole ratios was as follows:

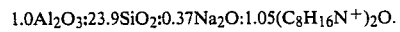
1.0Al$_2$O$_3$:23.9SiO$_2$:0.37Na$_2$O:1.05(C$_8$H$_{16}$N$^+$)$_2$O.

The as-synthesized LZ-133 exhibited the X-ray powder diffraction pattern of Table V. This pattern is essentially the same as the patterns of all other uncalcined zeolite LZ-133 compositions which are in the mixed sodium and methylquinuclidine cation form.

TABLE V

| 2θ | d, (A) | I/I° |
|---|---|---|
| 7.7 | 11.5 | 6 |
| 9.8 | 9.03 | 9 |
| 12.1 | 7.31 | 9 |
| 13.5 | 6.56 | 31 |
| 13.8 | 6.42 | 26 |
| 14.2 | 6.24 | 24 |
| 14.6 | 6.07 | 10 |
| 16.2 | 0.47 | 11 |
| 17.2 | 5.16 | 32 |
| 17.8 | 4.98 | 6 |
| 18.1 | 4.90 | 8 |
| 18.5 | 4.80 | 18 |
| 19.3 | 4.60 | 100 |
| 19.8 | 4.48 | 34 |
| 20.9 | 4.25 | 9 (sh) |
| 20.6 | 4.31 | 9 |
| 21.4 | 4.15 | 20 |
| 22.8 | 3.90 | 24 |
| 23.4 | 3.80 | 13 |
| 24.3 | 3.66 | 62 |
| 24.9 | 3.58 | 11 |
| 25.8 | 3.45 | 28 |
| 27.2 | 3.28 | 23 |
| 27.8 | 3.21 | 29 |
| 28.4 | 3.14 | 26 |
| 28.6 | 3.12 | 27 |
| 29.6 | 3.02 | 27 |
| 30.3 | 2.905 | 6 |
| 31.0 | 2.885 | 2 |
| 32.2 | 2.780 | 4 |
| 32.9 | 2.722 | 3 |
| 33.8 | 2.652 | 8 |
| 34.9 | 2.571 | 2 |

TABLE V-continued

| 2θ | d, (Å) | I/I° |
|---|---|---|
| 35.8 | 2.321 | 11 |

(c) A portion of the crystalline LZ-133 obtained in part (b) of this Example 1 was calcined in air at 600° C. for 2 hours. The calcined product had an X-ray powder diffraction pattern characterized by the following data.

This pattern is essentially the same as the patterns of all other zeolite LZ-133 compositions which have been calcined at above 500° C. for a sufficient time to be free of organic cations and whose metal cations consist of sodium cations

| 2θ | d, | I/IO |
|---|---|---|
| 7.7 | 11.5 | 20 |
| 8.1 | 10.9 | 18 |
| 9.8 | 9.03 | 33 |
| 12.1 | 7.31 | 28 |
| 13.7 | 6.46 | 100 |
| 13.9 | 6.37 | SH |
| 14.2 | 6.24 | 67 |
| 14.7 | 6.03 | 10 |
| 16.2 | 5.47 | 7 |
| 17.3 | 5.13 | 14 |
| 17.9 | 4.96 | SH |
| 18.1 | 4.90 | 9 |
| 18.6 | 4.77 | 12 |
| 19.4 | 4.58 | 91 |
| 19.9 | 4.46 | 37 |
| 20.7 | 4.29 | 8 |
| 21.5 | 4.13 | 16 |
| 23.0 | 3.87 | 20 |
| 23.7 | 3.75 | 11 |
| 24.5 | 3.63 | 65 |
| 24.9 | 3.58 | SH |
| 25.9 | 3.44 | 30 |
| 27.4 | 3.26 | 27 |
| 28.1 | 3.18 | 33 |
| 28.5 | 3.13 | 29 |
| 28.7 | 3.11 | 30 |
| 29.7 | 3.01 | 36 |
| 30.4 | 2.940 | 7 |
| 31.0 | 2.885 | 5 |
| 32.3 | 2.772 | 6 |
| 32.8 | 2.730 | 6 |
| 33.6 | 2.667 | SH |
| 34.0 | 2.637 | 11 |
| 35.0 | 2.564 | 6 |
| 36.0 | 2.495 | 32 |

(SH = shoulder)

(SH = shoulder)

(d) Adsorption capacities were measured on the calcined product using a standard McBain-Bakr gravimetric adsorption apparatus. The following data were obtained on samples activated at 350° C. under vacuum for 16 hours.

| | Kinetic Diameter (Å) | Pressure (torr) | Temp. (°C.) | Wt. % Adsorbed |
|---|---|---|---|---|
| O2 | 3.46 | 97.0 | −183 | 12.0 |
| O2 | 3.46 | 502 | −183 | 14.4 |
| n-hexane | 4.3 | 99.0 | 23 | 4.8 |
| n-butane | 4.3 | 760 | 23 | 1.42* |
| iso-butane | 5.0 | 504 | 23 | 0.67 |
| H2O | 2.65 | 4.6 | 23 | 10.8 |
| H2O | 2.65 | 19.0 | 23 | 19.4 |

*After 6.5 hours

The pore size of the calcined product is 4.3 Å as shown by adsorption of n-hexane (kinetic diameter of 4.3 Å) and nil adsorption of iso-butane (kinetic diameter of 5.0 Å). Neither the as-synthesized or any other cation form, including the decationized form, of LZ-133 is capable of adsorbing into the intracrystalline cavities thereof, molecules of cyclohexane, for the reason that the kinetic diameter of cyclohexane (6.0 Å) is to large to pass through any of the pore openings of the crystal lattice.

EXAMPLES 2-4

Using synthesis procedures similar to those detailed in Example 1, supra, three additional preparations or LZ-133 were made using the reagents and conditions set forth in tabular form below. In all preparations., the product was LZ-133 along with a small amount of zeolite LZ-132 as an impurity component. LZ-132 is described in detail in copending application Ser. No. 363,110 filed contemporaneously with the present application.

TABLE V

| | Synthesis Gel Composition Oxide Mole Ratio | | | | | Temp. | Time | Product Composition, Oxide Mole Ratio | | | |
|---|---|---|---|---|---|---|---|---|---|---|---|
| Example | $Al_2O_3$ | $SiO_2$ | $Na_2O$ | $H_2O$ | MeQI | °C. | (hrs.) | $Al_2O_3$ | $SiO_2$ | $Na_2O$ | $R_2O$ |
| 2 | 1.0 | 40.0 | 4.5 | 420 | 5.6 | 200 | 24 | 1.0 | 30.7 | 0.35 | 1.3 |
| 3 | 1.0 | 50.0 | 5.0 | 500 | 8.0 | 200 | 47.5 | 1.0 | 45.1 | 0.44 | 1.5 |
| 4 | 1.0 | 27.3 | 2.64* | 420 | 5.6 | 200 | 48 | 1.0 | 23.2 | 0.09** | 0.99 |

*Plus 1.3 $Cs_2O$
**Plus 0.42 $Cs_2O$

EXAMPLE 5

In order to demonstrate the catalytic activity of zeolite LZ-133, a sample was employed as the catalyst in the catalytic cracking of n-butane. The sample selected was the product of Example 2, above, which had been washed with sodium hydroxide solution followed by washing with hydrochloric acid and subsequent calcination at 600° C. About 5 grams of the sample (20–40 U.S. Standard mesh) was placed in a ½-inch O.D. quartz tube reactor and activated in situ for 60 minutes at 500° C. in a flowing (200 cm³/min.) stream of dry helium. Thereafter a feedstock consisting of a mixture of 2 mole-% n-butane in helium was passed over the catalyst sample at the rate of 50 cm³/min. for a period of 40 minutes. The product stream was analyzed at 10-minute intervals. The pseudo first-order reation rate constant ($k_a$) was then calculated to determine the catalytic activity of the zeolite LZ-133. The $k_a$ value for the calcined LZ-133 sample was found to be 3.8 as compared to a $k_a$ value of 1.1 for NH4-Y zeolite.

The hydrophobic surface characteristics of LZ-133 are very similar to those of LZ-132. The characteristics of the latter zeolite, in this regard, were demonstrated using an ethanol-water shake test. A one gram sample of a stepwise-calcined sample of Example 1(b) was added to a small serum bottle. The stepwise calcination procedure consisted of raising the sample temperature to 100° C., followed by a heat-up rate of 100° C./hr., with an intermittent holding time of one hour when the temperature reached 200°, 300°, 400° and 500° C., until the final temperature reached 590° C. During the heat-up time, the sample was under a nitrogen purge. When the temperature reached 590° C., 5.0 vol.-% of $C_2H_5OH$ in $H_2O$ solution was introduced. The bottle was sealed and shaken throughly. The liquid was analyzed by gas chromatography and the result indicated a total of 14.9% ethanol removal. For comparison, acid-washed silicalite removed 23% ethanol from the same solution.

What is claimed is:

1. Crystalline aluminosilicate zeolite composition having a chemical composition in terms of mole ratios of oxides:

$$x\ M_{2/n}O{:}Al_2O_3{:}y\ SiO_2{:}z\ H_2O$$

wherein "M" is at least one cation having the valence "n", "x" has a value of from zero to 3.5, "y" has a value of from 10 to 80 and "z" has a value from zero to 15, said aluminosilicate having an X-ray powder diffraction pattern which does not contain a d-spacing in the range of 4.01–4.03 A and containing at least the d-spacings set forth in Table III or Table IV, the pore diameters of said zeolite being about 4.3 A.

2. Crystalline aluminosilicate zeolite composition according to claim 1 wherein "y" has a value of from 15 to 50.

3. Crystalline aluminosilicate zeolite composition according to claim 1 which has an X-ray powder diffraction pattern containing at least the d-spacings set forth in Table III.

4. Crystalline aluminosilicate zeolite composition according to claim 1 which has an X-ray powder diffraction pattern containing at least the d-spacings set forth in Table IV.

5. Crystalline aluminosilicate zeolite composition having an as-synthesized chemical composition in terms of mole ratios of oxides:

$$a\ Q_{2/n}O{:}b\ R_2O{:}Al_2O_3{:}c\ SiO_2{:}d\ H_2O$$

wherein "a" has a value in the range of 0.1 to 1.5, Q is an alkali metal or alkaline earth metal cation having the valence of "n", "b" has a value in the range of 0.5 to 2.5, the value of (a+b) is from 0.9 to 3.5, "R" represents the methylquinuclidine ion, "c" has a value of from 10 to 80, "d" has a value of from zero to 15, said zeolite composition having an X-ray powder diffraction pattern which consists essentially of the d-spacings set forth in Table V, the pore diameters of said zeolite being about 4.3A.

6. Crystalline aluminosilicate zeolite composition according to claim 5 wherein "c" has a value of from 15 to 50.

7. Crystalline aluminosilicate composition according to claim 4 wherein "x" has a value of zero to 1.1 and "M" is a cation selected from the group consisting of ammonium, hydrogen or metal.

8. Crystalline aluminosilicate composition resulting from the calcination of the composition of claim 3 at a temperature of at least 400° C. up to the crystal destruction temperature thereof.

* * * * *